(12) United States Patent
Albrecht, Jr.

(10) Patent No.: US 10,209,229 B2
(45) Date of Patent: Feb. 19, 2019

(54) MIXER BYPASS SAMPLE INJECTION FOR LIQUID CHROMATOGRAPHY

(71) Applicant: Agilent Technologies, Inc., Santa Clara, CA (US)

(72) Inventor: Robert William Albrecht, Jr., Kennett Square, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/910,414

(22) Filed: Mar. 2, 2018

(65) Prior Publication Data

US 2018/0196018 A1   Jul. 12, 2018

Related U.S. Application Data

(63) Continuation of application No. 14/648,065, filed as application No. PCT/US2013/067112 on Oct. 28, 2013, now Pat. No. 9,945,820.

(60) Provisional application No. 61/731,611, filed on Nov. 30, 2012.

(51) Int. Cl.
| | |
|---|---|
| *G01N 30/20* | (2006.01) |
| *G01N 30/34* | (2006.01) |
| *G01N 30/38* | (2006.01) |
| *G01N 30/02* | (2006.01) |
| *B01L 3/00* | (2006.01) |

(52) U.S. Cl.
CPC .............. *G01N 30/20* (2013.01); *G01N 30/34* (2013.01); *G01N 30/38* (2013.01); *B01L 3/502784* (2013.01); *G01N 2030/027* (2013.01); *G01N 2030/207* (2013.01); *G01N 2030/347* (2013.01)

(58) Field of Classification Search
CPC ........ G01N 30/20; G01N 30/34; G01N 30/38; G01N 2030/027; G01N 2030/207; G01N 2030/347; B01L 3/502784
See application file for complete search history.

(56) References Cited

U.S. PATENT DOCUMENTS

| | | |
|---|---|---|
| 3,940,994 A | 3/1976 | Klee et al. |
| 5,738,783 A | 4/1998 | Shirota et al. |
| 6,576,125 B2 | 6/2003 | Berger et al. |
| 7,687,269 B2 | 3/2010 | Kautz et al. |
| 8,047,060 B2 | 11/2011 | Dourdeville et al. |
| 2003/0034307 A1 | 2/2003 | Berger et al. |
| 2004/0092033 A1 | 5/2004 | Gustafson et al. |

(Continued)

FOREIGN PATENT DOCUMENTS

| | | |
|---|---|---|
| WO | 2004025272 A1 | 3/2004 |
| WO | 2005059512 A2 | 6/2005 |

OTHER PUBLICATIONS

International Search Report issued in counterpart International Application No. PCT/US2013/067112 dated Jun. 4, 2014 (six (6) pages).

(Continued)

*Primary Examiner* — David Bolduc

(57) ABSTRACT

In a liquid chromatography system, a sample is injected into a column by flowing a solvent mixture from a mixer into the column along a solvent mixture flow path; and injecting a sample into the solvent mixture flow path downstream of the mixer. In another liquid chromatography system, a sample is injected into a column by loading an isolator fluid into a sample loop, loading a sample into the sample loop, and flowing the sample into the column as a plug in front of the isolator fluid.

20 Claims, 3 Drawing Sheets

(56) References Cited

U.S. PATENT DOCUMENTS

| | | |
|---|---|---|
| 2005/0072671 A1 | 4/2005 | Rocklin et al. |
| 2005/0194298 A1 | 9/2005 | Usowicz et al. |
| 2008/0115568 A1 | 5/2008 | Lee et al. |
| 2008/0142444 A1 | 6/2008 | Toyosaki |
| 2009/0205409 A1 | 8/2009 | Ciavarini et al. |
| 2009/0294344 A1 | 12/2009 | Corral et al. |
| 2010/0043539 A1 | 2/2010 | Fadgen et al. |
| 2010/0107742 A1 | 5/2010 | Liu et al. |
| 2011/0049031 A1 | 3/2011 | Cappiello |
| 2011/0094606 A1 | 4/2011 | Kanomata et al. |
| 2012/0153143 A1 | 6/2012 | Kennedy et al. |
| 2012/0205314 A1 | 8/2012 | Davison |
| 2012/0287746 A1 | 11/2012 | Angelosanto et al. |
| 2012/0303167 A1 | 11/2012 | Heden et al. |

OTHER PUBLICATIONS

Keifer, Paul A.; "Flow injection analysis NMR (FIA-NMR): a novel flow NMR technique that complements LC-NMR and direct injection NMR (DI-NMR)", Magnetic Resonance in Chemistry, vol. 41, No. 7, May 19, 2003, pp. 509-516.

Masuda, Junichi et al.; "Fully automated micro-and nanoscale one-or two-dimensional high-performance liquid chromatography system for liquid chromatography-mass spectrometer compatible with non-volatile salts for ion exchange chromatography"; Journal of Chromatography, pp. 57-69 (2005).

MIXER BYPASS SAMPLE INJECTION FOR LIQUID CHROMATOGRAPHY

CROSS-REFERENCE TO RELATED APPLICATIONS

This application is a continuation application under 37 C.F.R. § 1.53(b) of U.S. patent application Ser. No. 14/648,065, filed on May 28, 2015; which is the national stage of International Application No. PCT/US2013/067112, filed on Oct. 28, 2013, titled MIXER BYPASS SAMPLE INJECTION FOR LIQUID CHROMATOGRAPHY, which claims priority of U.S. Application Ser. No. 61/731,611, filed on Nov. 30, 2012, titled MIXER BYPASS SAMPLE INJECTION FOR LIQUID CHROMATOGRAPHY; the contents of each of which applications are incorporated by reference herein in their entireties.

TECHNICAL FIELD

The present invention relates generally to liquid chromatography, including high performance liquid chromatography (HPLC) and supercritical fluid chromatography (SFC), and in particular relates to sample injection in systems implementing liquid chromatography.

BACKGROUND

Liquid chromatography (LC) is a technique for performing an analytical or preparative separation of a liquid-phase sample material of interest (e.g., a mixture of different chemical compounds) into constituent components. During the course of a chromatographic separation, the sample material is transported in a mobile phase (typically one or more solvents). The sample (the sample material and mobile phase in which it is dissolved) is forced through a stationary phase that is immiscible with the mobile phase. Typically, the stationary phase is provided in the form of a mass of particles (a packing or bed) supported in a column or cartridge through which the sample flows. The column bed is typically retained at each end of the column by a frit or filter that allows the sample to flow through while preventing the packing material from escaping the column. The respective compositions of the mobile phase and stationary phase are selected to cause differing components of the sample material in the column to become distributed between the mobile phase and stationary phase to varying degrees dependent on the respective chemistries of the sample material's components. Components that are strongly retained by the stationary phase travel slowly with the mobile phase, while components that are weakly retained by the stationary phase travel more rapidly. As a result, components of differing compositions become separated from each other as the mobile phase flows through the column.

In analytical separation, the components are separated to facilitate their analysis by detection and data acquisition techniques. Analytical separation typically entails the use of a small amount of material and small inside-diameter columns (e.g, less than 1 inch). In preparative separation, the components are separated to purify or isolate one or more chemical components from the starting material, which may be done for a further use such as reaction, synthesis, etc. Preparative separation may be performed on a small scale comparative to analytical separation, or may be performed on a much larger scale to purify a large quantity of sample material, and thus may utilize larger inside-diameter columns (e.g., 1-24 inches).

Typically, a sample to be separated is introduced into a column by first injecting the sample into a solvent flow stream at a point upstream of the column. The solvent flow stream may be a mixed flow stream formed by mixing the flows of a weak solvent and a strong solvent (or "modifier" solvent) in a solvent mixer upstream of the column. In this case, the sample may be injected into the mixed flow stream, i.e., downstream from the mixer. Typically, the sample is injected into the column with the strong solvent still being at a high concentration, which may cause chromatographic band broadening relative to the amount of solvent injected with the sample, and thus poor resolution, especially in preparative chromatography where larger quantities of sample are employed. The addition of a relatively weak solvent may be done to mitigate the effects of the strong solvent, but can cause the sample to crystallize in the sample loop or other tubing and clog the system.

Alternatively, the sample may be injected into the flow path of the strong solvent before the strong solvent is merged with the weak solvent in the mixer. In this case, the sample flows through the mixer before flowing into the column. This is disadvantageous because the sample may be retained by the mixer, thus contaminating the mixer and causing unwanted sample dispersion upstream of the column. Moreover, avoiding sample retention by the mixer means limiting the choice of materials utilized to construct the mixer. Additionally, in this case the strong solvent (usually methanol or acetonitrile) serves as the injection solvent for the sample. Many samples, however, are dissolved in other solvents such as dimethyl sulfoxide (DMSO), which might make a better injection solvent in certain applications. Moreover, DMSO and other sample solvents are often incompatible with the materials constituting the mixer's structure. Also, by utilizing the strong solvent as the injection solvent, the rate at which the sample is injected into the column is limited by the practical flow rates of the pump employed for flowing the strong solvent.

Another problem with known techniques for sample injection in high-pressure systems is that the sample is compressed in the sample loop or tubing due to operation of the pump. This compression can cause a pressure shock that disturbs the column bed, which may produce undesirable voids in the bed and loosen stationary phase material.

In addition, the use of a separate sample injection pump can cause carryover without much rinsing, because samples will diffuse into the sample push solvent and the walls of the injector are not sufficiently cleaned by injection solvent alone. The volume of the sample injection pump adds compliance to the system and increases the pressure shock that occurs when the sample injection pump is switched in-line with a high-pressure flow stream.

Therefore, there is a need for injecting samples into an LC column while minimizing sample dispersion upstream of the LC column. There is also a need for bypassing the solvent mixer to prevent mixer contamination with the sample or the solvent in which the sample is dissolved.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a liquid chromatography (LC) system includes: a column; a first solvent source; a second solvent source; a mixer communicating with the first solvent source via a first solvent line, with the second solvent source via a second solvent line, and with the column via a solvent mixture line; a fluidic junction in solvent mixture line; and an injection valve comprising a sample loop and communicating with the fluidic junction and an injection solvent source, wherein the injection valve is adjustable to a sample injection position that defines a flow path for an injection solvent through the sample loop and to the fluidic junction, such that the injection solvent carries a sample in the sample loop into the solvent mixture line downstream from the mixer.

According to another embodiment, a liquid chromatography (LC) system includes: a column; a sample source; an isolator fluid source; an injection valve comprising a sample loop and communicating with the sample source, the isolator fluid source, and a sample injection line leading to the column, wherein the injection valve is adjustable to an isolator fluid load position that defines a flow path for an isolator fluid to be flowed from the isolator fluid source into the sample loop; and a fluid moving device communicating with the sample loop and configured for selectively pulling fluid into the sample loop and pushing fluid out from the sample loop.

According to another embodiment, a method for injecting a sample into a liquid chromatography column includes: flowing a first solvent and a second solvent into a mixer to form a solvent mixture; flowing the solvent mixture into the column along a solvent mixture flow path; and while flowing the solvent mixture, injecting a sample comprising a sample material carried in an injection solvent into the solvent mixture flow path at a point between the mixer and the column.

According to another embodiment, a method for injecting a sample into a liquid chromatography column includes: loading an isolator fluid into a sample loop; loading a sample into the sample loop, the sample comprising a sample material carried in an injection solvent; and injecting the sample into the column by flowing the sample as a plug in front of the isolator fluid.

According to another embodiment, a liquid chromatography system is configured for performing any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

The present disclosure is directed to liquid chromatography (LC) systems, including both low-pressure and high-pressure LC systems. For convenience, in the present disclosure the term "liquid" encompasses not only liquids as conventionally defined (e.g., in the liquid phase region of pressure-temperature space) but also supercritical and near supercritical fluids. As used herein, a "near supercritical" fluid is a fluid at a pressure and/or temperature state that places the fluid outside of, but near to, the supercritical region of a pressure-temperature phase diagram for that fluid. A near supercritical fluid may, for example, be a highly compressed liquid at a temperature less than the critical temperature demarcating the supercritical phase. The terms "low-pressure" and "high-pressure" are used herein in a relative sense to describe the pressure at which a liquid flows in an LC system, including the flow through a chromatography column of the system. As non-limiting examples, low-pressure flow may range from 0 bar to 20 bar and high-pressure flow may range from 20 bar or greater. In the case of supercritical fluid chromatography (SFC), high-pressure flow may range from 50 bar or greater.

Non-limiting examples of LC systems are described below and illustrated in FIGS. 1 to 3. Such systems, when configured for high-pressure LC, may be configured for high performance liquid chromatography (HPLC), ultra high performance liquid chromatography (UHPLC), or SFC. In various embodiments, the systems described herein may be configured for analytical chromatography or preparative chromatography. In various embodiments, the systems described herein may be configured for normal-phase chromatography, reversed-phase chromatography, or other types of chromatography involving the flow of a sample-bearing mobile phase through a column containing a packing or bed supporting a stationary phase. The systems described herein may further be configured for isocratic elution or gradient elution, and may be switchable between these two modes of operation. The structure and operation of various types of LC systems entailing the low-pressure or high-pressure flow of liquids and supercritical fluids, and of the individual components typically utilized in such systems, are generally understood by persons skilled in the art, and thus will be described only briefly as necessary for understanding the presently disclosed subject matter. It is also understood by persons skilled in the art that the choice of certain components may depend on whether the system operates in a low-pressure or high-pressure flow regime, or on the type of LC being performed.

Figure 1:
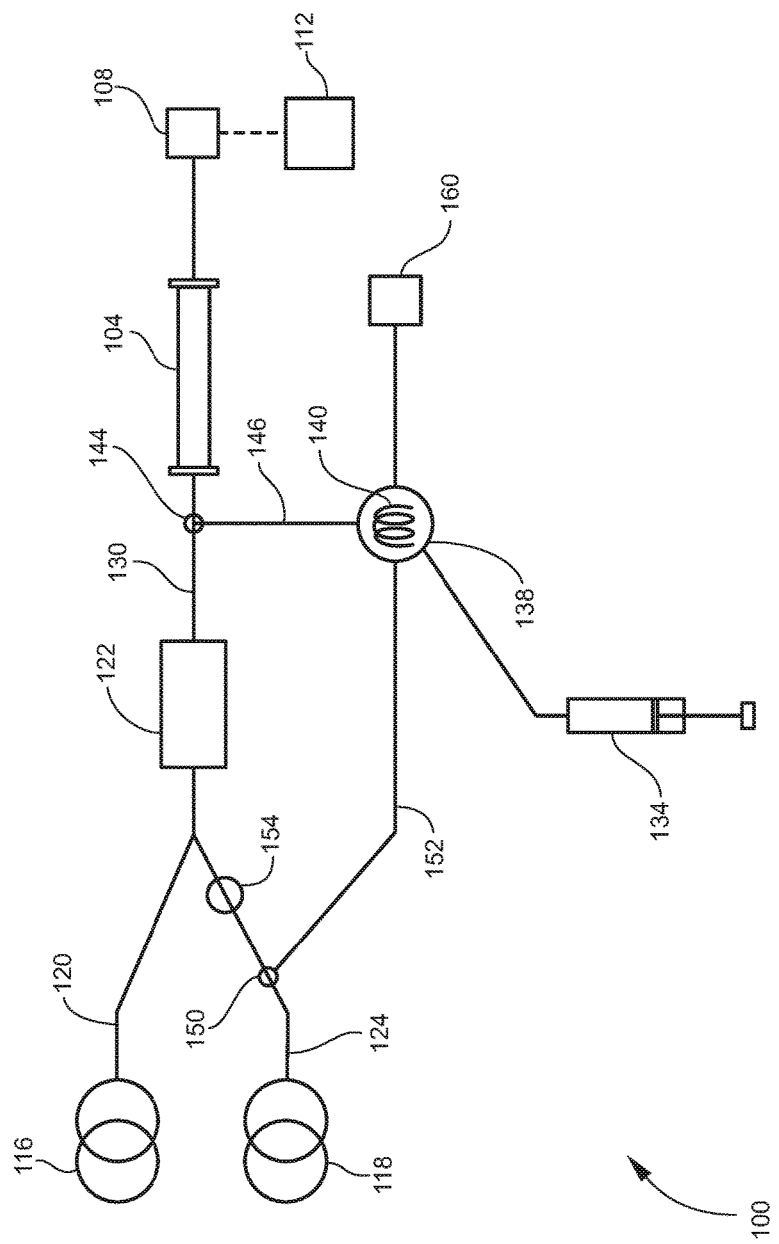
FIG. 1 is a schematic view of an example of a liquid chromatography system according to one embodiment.

FIG. 1 is a schematic view of an example of an LC system 100 according to one embodiment. The system 100 may generally include a chromatography column 104, a source of one or more solvents upstream of the column 104 for use as a mobile phase, a sample injection system for introducing a sample (sample material dissolved in a sample solvent) into the solvent flow stream (upstream of the column 104 or at the column head), a collection site 108 downstream of the column 104 for collecting compounds separated by the column 104, and a system controller 112. The collection site 108 may include a detector for detecting the compounds as they elute from the column 104. The detector may be any type suitable for enabling chromatographic peak data to be acquired and processed by the system controller 112.

In the present embodiment, the solvent source includes a first solvent source 116 and a second solvent source 118. The solvent sources 116 and 118 may schematically represent solvent reservoirs, solvent pumps, and associated hardware for supplying a first solvent (or "A" solvent) and a second solvent (or "B" solvent), respectively. Examples of solvent pumps include, but are not limited to, metering, single or multiple piston, gear, peristaltic, and bellows pumps. For SFC, the first solvent source 116 is adapted for controlling temperature and pressure as needed to maintain the first solvent in or near a supercritical state. The first solvent may be a relatively weak solvent and the second solvent may be a relatively strong solvent. In the context of the present disclosure, a "weak" solvent is one for which a sample component has relatively lesser affinity as compared to the stationary phase in the column 104, and a "strong" solvent is one for which the sample component has relatively greater affinity as compared to the stationary phase. Thus, a sample component carried in a weak solvent will be strongly retained on the stationary phase, resulting in a longer time of elution from the column 104. By comparison, a sample component carried in a strong solvent will be weakly retained (or not retained at all) on the stationary phase, resulting in a shorter time of elution from the column 104. The respective compositions of the first solvent and second solvent will generally depend on the sample material being processed and the type of chromatography being implemented. Examples of weak solvents include, but are not limited to, water and aqueous buffer fluids for reversed phase LC, non-polar solvents such as hexane and heptanes for normal phase LC, and supercritical or near supercritical fluids (typically carbon dioxide). The strong solvent (or "modifier" solvent) is typically an organic solvent. Examples of strong solvents include, but are not limited to, alcohols such as methanol, ethanol, and isopropyl alcohol; or any polar solvent such as acetonitrile; chloroform; tetrahydrofuran (THF); dimethyl sulfoxide (DMSO), and dimethylformamide (DMF). In a common (yet non-limiting) example of SFC, the first solvent is supercritical or near supercritical carbon dioxide, and the second solvent is methanol or another polar solvent. Solvents other than carbon dioxide that are usable in a supercritical or near supercritical state may be suitable, one non-limiting example being propane. In other embodiments, more than two solvent sources may be provided.

The first solvent is flowed from the first solvent source 116, through a first solvent line 120 and into a solvent mixer 122. The second solvent is flowed from the second solvent source 118, through a second solvent line 124 and into the mixer 122. As used throughout the present disclosure, the term "line" encompasses any fluid conduit (or tubing) having a chemical inertness and pressure rating suitable for LC. The mixer 122 may be any chamber or column of sufficient length and volume to achieve mixing of the first solvent and second solvent to a level of homogeneity suitable for the application. The mixer 122 includes at least one mixer inlet and at least one mixer outlet. By example, FIG. 1 schematically depicts the first solvent line 120 and second solvent line 124 merging at a point upstream of the mixer 122, with a common line communicating with a single mixer inlet. Alternatively, the first solvent line 120 and second solvent line 124 may communicate directly with the mixer 122 at individual mixer inlets. The mixer 122 establishes a solvent mixture flow stream (or flow path), which flows from the mixer outlet and through a solvent mixture line 130 communicating with a column inlet of the column 104.

The sample injection system may include a sample injection device and a sample source 134. In some embodiments, the sample injection device is or includes a multi-port injection valve 138. As appreciated by persons skilled in the art, the injection valve 138 may include a stationary portion containing internal passages and a movable (rotary or linear) portion containing external ports. The movable portion may be movable in an indexed manner to a plurality of valve positions, and may be powered by a stepper motor. Typically, at each valve position, two of the external ports are placed in fluid communication with one of the internal passages. Thus, selecting different valve positions enables selecting different pairs of ports to serve as a fluid inlet and outlet, thereby selecting different fluid pathways between components external to the injection valve 138 that are in fluid communication with the ports. Two of the ports may communicate with a sample loop 140. Depending on design the sample loop 140 may be external or internal to the valve structure, in either case having a length sufficient for holding a desired volume of fluid. As examples, an external loop may be any coiled or uncoiled section of tubing, and an internal loop may be an internal tube or channel formed in the valve structure. The sample loop 140 (and other lines or tubing of the system 100) may be lined with silanized glass or a fluorous polymer such as PTFE (polytetrafluoroethylene).

One of the ports communicates with a first fluidic junction 144 (e.g., a tee connection) via a sample injection line 146. The first fluidic junction 144 is positioned in the solvent mixture line 130 between the mixer 122 and the column 104, and may be positioned just upstream of the column 104. The sample injection line 146 may have a smaller inside diameter relative to other tubing utilized in the system 100 to minimize the swept volume of the sample injection line 146 and make cleaning it easier. Another port of the injection valve 138 communicates with a second fluidic junction 150 via an injection solvent line 152. The second fluidic junction 150 is positioned in the second solvent line 124 between the second solvent source 118 and a flow restrictor 154. The flow restrictor 154, also positioned in the second solvent line 124, may be any device suitable for limiting the flow of the second solvent in the direction of the mixer 122. As examples, the flow restrictor 154 may include one or more orifice plates in the second solvent line 124, or may include a valve switchable between ON and OFF positions and in some embodiments to intermediate positions between ON and OFF positions.

Another port of the injection valve 138 communicates with the sample source 134. The sample source 134 may be an injection needle, cannula or reservoir containing a sample material dissolved in an appropriate solvent (or "sample solvent"). In some embodiments, the injection needle, cannula or reservoir is part of, or communicates with, a pump such as a syringe pump as illustrated in FIG. 1. The syringe pump may include a piston that may be manually actuated or powered by a stepper motor. Another port of the injection valve 138 may communicate with a waste receptacle 160.

The injection valve 138 is adjustable (movable, e.g., rotatable or slidable) to a plurality of different valve positions, including a sample load position, a sample injection position, and a rinse position. As one example of a sample load position, the injection valve 138 is adjusted to establish a flow path from the sample source 134, through the sample loop 140, and into the waste receptacle 160. The syringe pump (or other fluid moving device) may then be operated to push a desired amount of the sample into the sample loop 140, with any excess sample collected at the waste receptacle 160. At the sample injection position, the injection valve 138 establishes a flow path from the second solvent source 118 into the injection solvent line 152 via the second fluidic junction 150, through the sample loop 140 and sample injection line 146, and into the solvent mixture line 130 via the first fluidic junction 144. The rinse position may correspond to one or more positions at which a selected port is placed in communication with the port leading to the waste receptacle 160, for the purpose of running a rinse solvent through the sample loop 140 and one or more internal passages of the injection valve 138.

An example of a method for injecting a sample into the column 104 will now be described. In this example, the system is configured as described above and illustrated in FIG. 1. The injection valve 138 and associated plumbing may be first be primed with an injection solvent, such as by setting the injection valve 138 to the sample injection position and operating the second solvent source 118 to fill or partially fill an internal volume of the injection valve 138, the sample loop 140, and the sample injection line 146 with the second solvent. The injection valve 138 may then be switched to the sample load position to flow sample (i.e., a matrix of sample material and sample solvent) into the sample loop 140 as described above. The sample solvent in which the sample material is initially provided may be the same as or different than the second solvent. Before, during or after priming, or before, during or after sample loading, a flow of solvent mixture into the column 104 is established by operating the solvent sources 116 and 118 to pump the first solvent and second solvent into the mixer 122 as described above. The pumps associated with the first solvent source 116 and second solvent source 118 are controlled as necessary to maintain a desired (i.e., predetermined) flow rate of the solvent mixture and respective concentrations of the first solvent and second solvent in the solvent mixture. Operation of the pump of the second solvent source 118 may fill or partially fill the injection solvent line 152 via the second fluidic junction 150.

After establishing the solvent mixture flow, and with the sample having been loaded in the sample loop 140, the injection valve 138 may be switched to the sample injection position. At this position, a portion of the second solvent readily flows through the injection solvent line 152 and into the sample loop 140. The flow restrictor 154 in the second solvent line 124 upstream of the second fluidic junction 150 ensures that a portion of the second solvent flow is diverted to the injection valve 138 in this manner. As noted above, the flow restrictor 154 may or may not be adjustable. The flowing second solvent pushes the sample from the sample loop 140 through the sample injection line 146, and into the solvent mixture line 130 via the first fluidic junction 144. Consequently, the sample is injected into the column 104 with the solvent mixture. Chromatographic separation, detection and data acquisition (or collection of a purified target compound in the case of preparative chromatography) may then occur in a manner appreciated by persons skilled in the art.

From the foregoing, it can be seen that the sample injection flow path bypasses the solvent mixer 122. In this manner the sample does not contaminate, and is not dispersed by, the mixer 122. Bypassing the mixer 122 thus avoids the band broadening effects attributed to running the sample through the mixer 122, and improves peak resolution. Moreover, bypassing the mixer 122 enables a wider variety of materials to be selected for the mixer 122, as neither the sample material nor the sample solvent in which the sample material is initially dissolved comes into contact with the mixer 122. For instance, mixer materials that include active components or seals or other polymers may be utilized in the above-described embodiment. This may be particularly useful in the case of preparative chromatography, which often involves samples dissolved in solvents (e.g., DMSO) that are incompatible with many materials. In addition, the mixer 122 does not need to be completely swept by solvent to avoid cross-contamination between trace amounts of different samples. In addition, samples may be pushed from the sample loop 140 with 100% modifier solvent to prevent crystallization inside the injection valve 138. Modifier solvent usually dissolves samples better than the weaker solvents often employed with samples.

Continuing with FIG. 1, the system controller 112 is schematically depicted as representing one or more modules configured for controlling, monitoring and/or timing various functional aspects and components of the system 100 such as, for example, operation of the solvent sources 116 and 118 (including adjustment of flow rate and/or pressure, and solvent gradient programming if applicable), adjustment of the flow restrictor 154 (if adjustable), adjustment of the injection valve 138 to various positions, operation of the syringe pump or other fluid moving device, and operation of the detector (if included). The system controller 112 may also be configured for receiving the detection signals from the detector and performing other tasks relating to data acquisition and signal analysis as necessary to generate a chromatogram or other output characterizing the sample under analysis. The system controller 112 may include a computer-readable medium that includes instructions for performing all or part of any of the methods disclosed herein. For convenience, the system controller 112 is schematically illustrated as being in signal communication with the detector (at the collection site 108), but it will be understood that the system controller 112 may be in signal communication with various components of the system 100 for purposes such as just noted. Signal communication may occur via wired or wireless communication links. Also for these purposes, the system controller 112 may include one or more types of hardware, firmware and/or software, as well as one or more memories and databases. The system controller 112 typically includes a main electronic processor providing overall control, and may include one or more electronic processors configured for dedicated control operations or specific signal processing tasks. The system controller 112 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The system controller 112 may include an operating system (e.g., Microsoft Windows® software) for controlling and managing various functions of the system controller 112.

Figure 2:
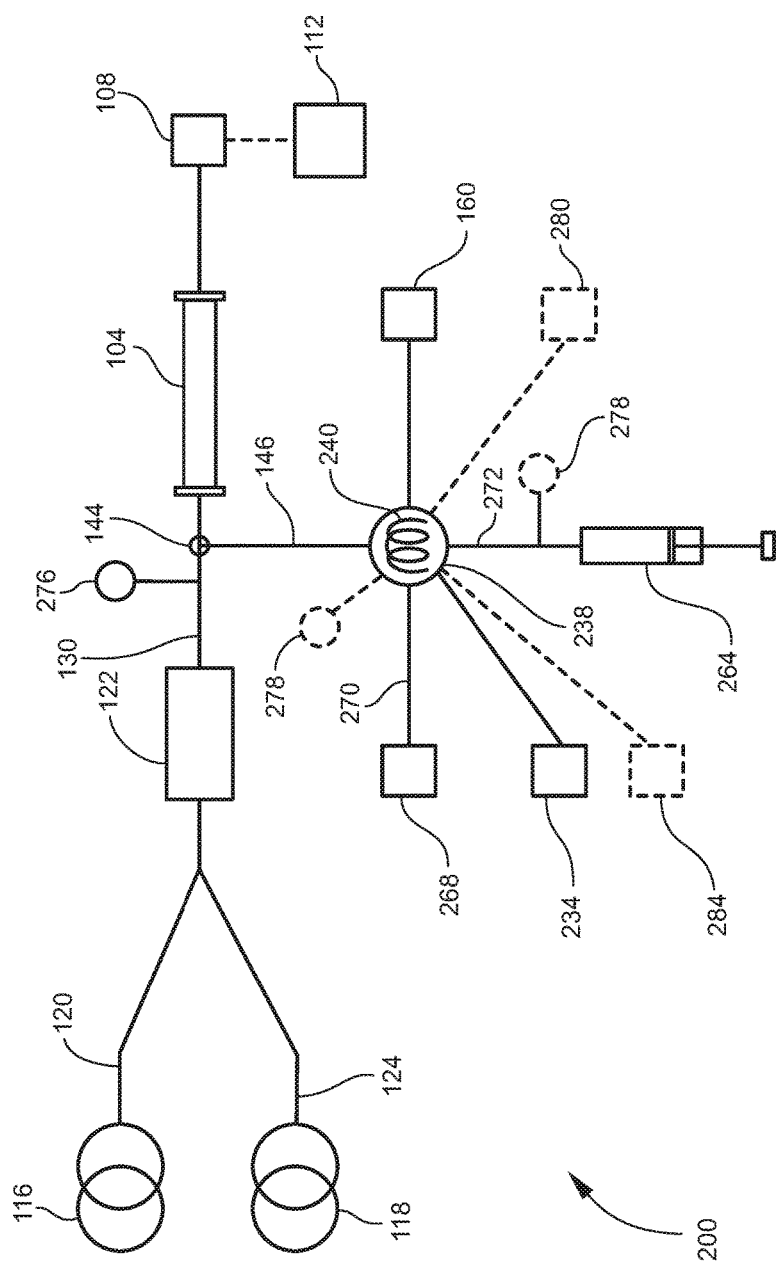
FIG. 2 is a schematic view of an example of a liquid chromatography system according to another embodiment.

FIG. 2 is a schematic view of an example of an LC system 200 according to another embodiment. Various components of the system 200 may be the same as or similar to components of the system 100, and are designated by the same or similar reference numerals in FIG. 2. Accordingly, the system 200 may generally include a chromatography column 104, a source of one or more solvents upstream of the column 104 for use as a mobile phase, a sample injection system for introducing a sample into the solvent flow stream, a collection site 108 downstream of the column 104 for collecting compounds, and a system controller 112. The collection site 108 may include a detector as noted above. The system controller 112 may be configured for controlling, monitoring and/or timing various functional aspects and components of the system 200, as generally described above.

In the present embodiment, the system 200 includes a first solvent source 116 and a second solvent source 118. The first solvent may be a relatively weak solvent and the second solvent may be a relatively strong solvent. The first and second solvents may be solvents such as given by example earlier in this disclosure. The first solvent is flowed from the first solvent source 116, through a first solvent line 120 and into a mixer 122. The second solvent is flowed from the second solvent source 118, through a second solvent line 124 and into the mixer 122. The mixer 122 includes at least one mixer inlet and at least one mixer outlet. The mixer 122 establishes a solvent mixture flow stream (or flow path), which flows from the mixer outlet and through a solvent mixture line 130 communicating with a column inlet of the column 104. More than two solvent sources may be provided as noted above.

The sample injection system may include a sample injection device, a sample source 234, and a fluid moving device such as a pump 264. In some embodiments, the sample injection device is or includes a multi-port injection valve 238, the structure and operation of which are generally described above. Two of the ports may communicate with an external or internal sample loop 240. One of the ports communicates with a fluidic junction 144 via a sample injection line 146. The fluidic junction 144 is positioned in the solvent mixture line 130 between the mixer 122 and the column 104, and may be positioned just upstream of the column 104. Another port of the injection valve 238 may communicate with an injection solvent source 268 via an injection solvent line 270. In some embodiments, the injection solvent may be the same as the second solvent supplied by the second solvent source 118, or may be the same as the sample solvent in which the sample material is initially supplied from the sample source 234. In some embodiments in which the injection solvent is the same as the second solvent, the second solvent source 118 may supply the solvent to the injection valve 238 in the same or similar manner as described above in conjunction with FIG. 1, i.e., by diverting a portion of the solvent flow from the second solvent source 118.

Another port of the injection valve 238 may communicate with the pump 264 via a pump line 272. The pump 264 may, for example, be a syringe pump that includes a piston that is manually actuated or powered by a stepper motor. In some embodiments, the pump line 272 may serve as the sample loop 240, in which case the sample loop 240 may be interconnected between the pump 264 and one port of the injection valve 238. Another port of the injection valve 238 may communicate with the sample source 234. The sample source 234 may be an injection needle, cannula or reservoir containing a sample material dissolved in an appropriate sample solvent. In some embodiments, the injection needle, cannula or reservoir is part of, or communicates with, a pump such as a syringe pump. Another port of the injection valve 238 may communicate with a waste receptacle 160.

The injection valve 238 is adjustable to a plurality of different positions, including an injection solvent load position, a sample load position, a sample injection position, and a rinse position. The injection solvent load position may include one or more valve positions as desired for filling or partially filling the internal volume, the sample injection line 146, the sample loop 240, the pump line 272 (if separated from the sample loop 240, as illustrated), and the needle of the sample source 234. As examples, one injection solvent load position may define a flow path that enables injection solvent to be aspirated by the pump 264 from the injection solvent source 268, through the sample loop 240 and into the pump 264. Another injection solvent load position (which may be the same as the sample injection position) may define a flow path that enables the injection solvent to be pushed by the pump 264 through the sample loop 240 and into the sample injection line 146. As one example of a sample load position, the injection valve 238 is adjusted to establish a flow path from the sample source 234 into the sample loop 240. The pump 264 may then be operated to draw a desired amount of the sample into the sample loop 240. At the sample injection position, the injection valve 238 establishes a flow path from the pump 264, through the sample loop 240 and sample injection line 146, and into the solvent mixture line 130 via the fluidic junction 144. The rinse position may correspond to one or more positions at which a selected port is placed in communication with the port leading to the waste receptacle 160, for the purpose of running a rinse solvent through the sample loop 240 and one or more internal passages of the injection valve 238.

An example of a method for injecting a sample into the column 104 will now be described. In this example, the system is configured as described above and illustrated in FIG. 2. The injection valve 238 and associated plumbing may be first be primed with an injection solvent, such as by setting the injection valve 238 to one or more injection solvent load positions and operating the pump 264 as described above. The injection valve 238 may then be switched to the sample load position to flow sample into the sample loop 240 as described above. Before, during or after priming, or before, during or after sample loading, a flow of solvent mixture into the column 104 is established by operating the solvent sources 116 and 118, whereby the first solvent and the second solvent are pumped into the mixer 122 and mixed as described above.

After establishing the solvent mixture flow, and with the sample having been loaded in the sample loop 240, the injection valve 238 may be switched to the sample injection position. At this position, the pump 264 is operated to push the sample from the sample loop 240, through the sample injection line 146, and into the solvent mixture flow path via the fluidic junction 144. Consequently, the sample is injected into the column 104 with the solvent mixture. Chromatographic separation, detection and data acquisition (or collection) may then occur in a manner appreciated by persons skilled in the art.

Continuing with FIG. 2, in some embodiments the system 200 may include a device or means for pre-pressurizing the sample injection flow stream to match the pressure in the solvent mixture flow stream. Such pre-pressurizing (i.e., pressurizing before injection of the sample into the solvent mixture flow stream) may be implemented to eliminate the pressure shock caused by switching a low-pressure flow stream into a high-pressure flow stream. The device or means may include a first pressure transducer 276 positioned appropriately for sensing the pressure in the solvent mixture flow path, such as just upstream of the column 104 as illustrated in FIG. 1, and a second pressure transducer 278 positioned appropriately for sensing the pressure in the sample injection flow path. FIG. 2 illustrates a few non-limiting, alternative examples of positions of the second pressure transducer 278. In one example, the second pressure transducer 278 communicates with the pump line 272, which may correspond to the sample loop 240 in some embodiments as noted above. In this case, the injection valve 238 may be adjustable to a pressurization (or pre-pressurization) position at which the port communicating with the pump 264 communicates with another port that is plugged. In another example, the second pressure transducer 278 communicates directly with a valve port and thus also serves as the plug. In either case, after loading the sample and before injecting the sample, the sample injection flow stream may be pressurized by setting the injection valve 238 to the pressurization position and operating the pump 264 to impart force on the fluid in the interior of the injection valve 238. The pressurizing step may be monitored by the system controller 112, which compares measurement signals received from the first pressure transducer 276 and second pressure transducer 278. The system controller 112 may cease the pressurizing step upon determining that the pressure in the injection valve 238 matches or nearly matches the pressure in the solvent mixture line 130.

In some embodiments the system 200 may include an isolator fluid source 280 communicating with a port of the injection valve 238. The injection valve 238 is adjustable to an isolator fluid load position that defines a flow path for isolator fluid to be drawn (i.e., pulled, aspirated) by the pump 264 from the isolator fluid source 280 into the sample loop 240, and at least partially into the needle (or both needle and barrel) of the pump 264 if desired. The isolator fluid may be utilized with high effectiveness both as a fluid for pushing the sample as a well-defined plug through the sample injection path, and as a solvent for rinsing the inside walls of the sample injection path (e.g., sample loop 240, internal passages of injection valve 238, sample injection line 146). The isolator fluid may be any fluid suitable for creating a plug-flow interface between samples dissolved in either an aqueous or organic solvent. That is, the sample flows as a plug in front of the isolator fluid, i.e., with no (or negligible) diffusion into the isolator fluid such that there is a well-defined interface between the sample and the isolator fluid. Examples of suitable isolator fluids include, but are not limited to, perfluorinated solvents and highly fluorinated solvents, such as the Fluorinert® fluids commercially available from 3M Company, St. Paul, Minn. (e.g., perfluorohexane, or $C_6F_{14}$, designated FC-72 by 3M). Highly fluorinated solvents include fluorinated compounds with properties similar to perfluorinated compounds such as, for example, $C_6HF_{13}$ and $C_6ClF_{13}$. The isolator fluid may be loaded before loading the sample into the sample loop 240.

An example of a method for injecting a sample into the column 104 will now be described, in which pre-pressurization and isolator fluid are utilized. Initially, the injection valve 238 is moved to the injection solvent load position to fill the internal volume of the injection valve 238 and at least partially fill the sample injection line 146. The injection valve 238 is then moved to the isolator fluid load position to fill the sample loop 240 and at least part of the pump 264 with isolator fluid. The injection valve 238 is then moved to the sample load position to draw (i.e, pull or aspirate) an amount of sample into the sample loop 240. At some time before or during any of the foregoing steps, a solvent mixture flow into the column 104 is established as described above. The injection valve 238 is then moved to the pressurization position to pre-pressurize the sample injection flow path, which may entail matching the pressure in the sample injection flow path with the pressure in the solvent mixture line 130 as described above. The injection valve 238 is then moved to the injection position and the pump 264 is operated to deliver the pre-pressurized sample into the solvent mixture line 130 at a desired flow rate. The injection valve 238 may then be moved to the rinse position to deliver the remaining injection solvent to the waste receptacle 160, during which time the isolator fluid fills the internal volume of the injection valve 238 and a small amount of isolator fluid may be expelled to the waste receptacle 160. The injection valve 238 may then be moved back to the isolator fluid load position to replenish lost isolator fluid, i.e., the pump 264 may be operated to draw isolator fluid from the isolator fluid source 280. The system is then ready to load and inject additional samples if desired.

If dissimilar samples are being injected into the column 104, additional steps may be implemented to clean the fluid lines. Generally, this may entail adjusting the injection valve 238 to different positions and pushing the injection solvent and/or isolator fluid through the lines to be cleaned. As one example, the injection valve 238 is moved to the injection solvent load position (or isolator fluid load position) and the pump 264 draws a small amount (e.g., a few microliters) of injection solvent (or isolator fluid). The injection needle or other conduit associated with the sample source 134 is then moved to a waste position or receptacle 284. The injection valve 238 is then moved to the sample loading position to open the flow path to the injection needle, which is now at the waste receptacle 284. The pump 264 then delivers enough injection solvent (or isolator fluid) so that the entire injection needle is swept with injection solvent (or isolator fluid) and a small volume of injection solvent (or isolator fluid) is expelled to the waste receptacle 284. The pump 264 then reverses direction to pull the injection solvent (or isolator fluid) back out from the injection needle and into the sample loop 240, leaving air in the injection needle. The injection valve 238 is then moved to the injection solvent load position and draws enough injection solvent to fill the internal volume of the injection valve 238 and at least partially fill the sample injection line 146. In preparation for the next sample, the injection valve 238 is moved back to the sample loading position and expels enough injection solvent to bring the injection solvent to the tip of the injection needle.

It thus can be seen that, like in the case of the system 100 illustrated in FIG. 1, in the system 200 of FIG. 2 the sample injection flow path bypasses the solvent mixer 122, thereby avoiding contamination of the mixer 122 and avoiding restricting the choice of materials for the mixer 122. Moreover, the pump 264 may be operated to introduce the sample into the solvent mixture stream at a controllable flow rate, which may be slower than the typical flow rate of a standard HPLC pump if desired. In addition, in the case of preparative chromatography, the pump 264 makes repeated delivery of the same sample easier, particularly when purifying chiral compounds. In addition, an injection solvent different from a modifier solvent or second solvent may be employed to better keep the sample dissolved and avoid in-loop crystallization. For example, DMSO instead of methanol may be employed as the injection solvent. In addition, the use of a pump 264 filled with isolator fluid and a plug flow interface between the injection solvent and the pump 264 eliminates diffusion of the sample into the pump 264 or the pump's working solvent. The isolator fluid allows the sample loop 240 to be completely swept of sample material and injection solvent and greatly reduces, or even eliminates, the need to rinse the sample loop 240 with large amounts of solvent. In addition, in the case of preparative chromatography, sample recovery is greatly enhanced by the use of isolator fluid in the sample injection system because the internal walls of the sample loop 240 are completely swept and displaced by the isolator fluid, such that near 100% sample recovery is possible even with dissimilar samples. In addition, pre-pressurization of the sample injection path to match the pressure of the solvent mixture stream eliminates pressure shocks that may disturb the column packing.

Figure 3:
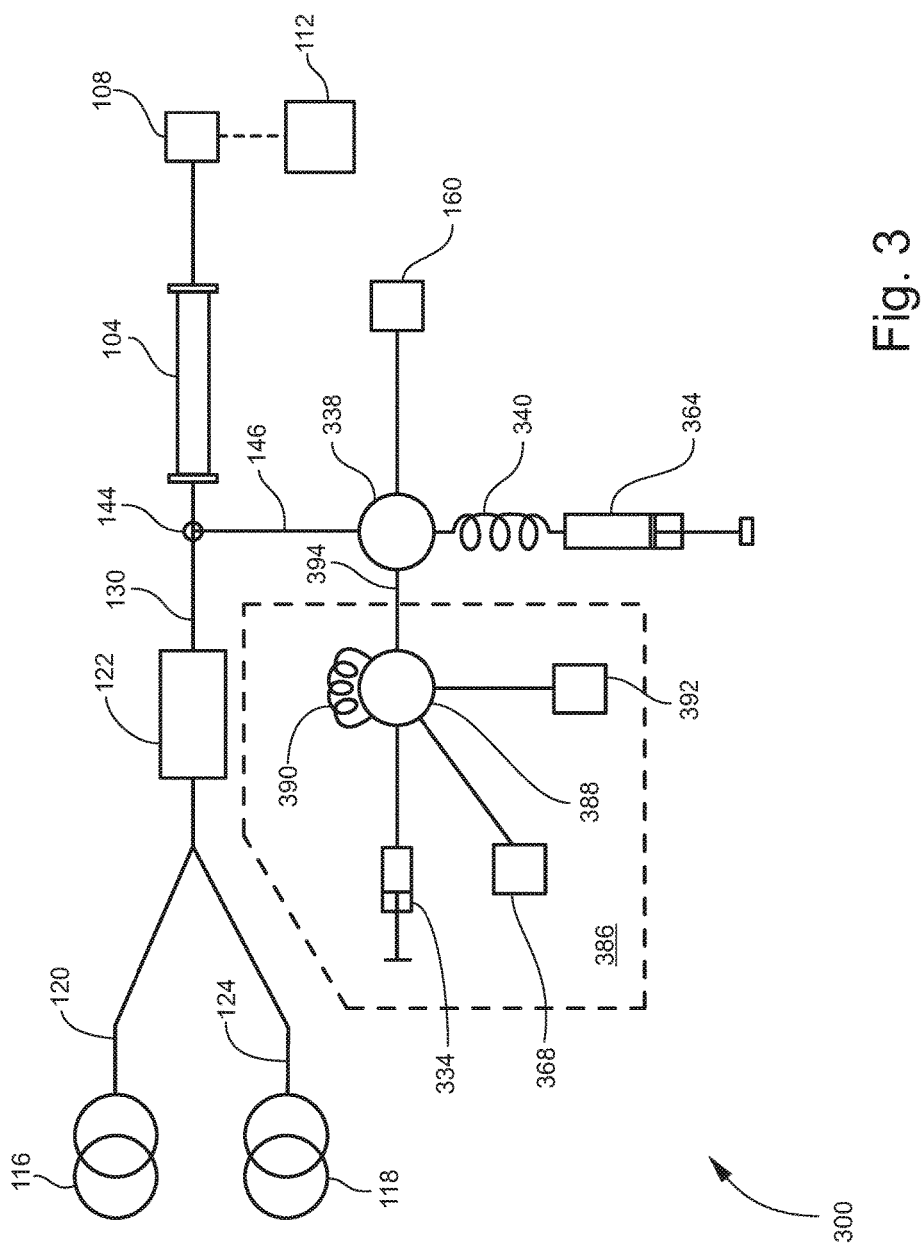
FIG. 3 is a schematic view of an example of a liquid chromatography system according to another embodiment.

FIG. 3 is a schematic view of an example of an LC system 300 according to another embodiment. Various components of the system 300 may be the same as or similar to components of the system 200, and are designated by the same or similar reference numerals in FIG. 2. Accordingly, the system 300 may generally include a chromatography column 104, a source of one or more solvents upstream of the column 104 for use as a mobile phase, a sample injection system for introducing a sample into the solvent flow stream, a collection site 108 downstream of the column 104 for collecting compounds, and a system controller 112. The collection site 108 may include a detector as noted above. The system controller 112 may be configured for controlling, monitoring and/or timing various functional aspects and components of the system 300, as generally described above.

In the present embodiment, the system 300 includes a first solvent source 116 and a second solvent source 118. The first solvent may be a weak solvent and the second solvent may be a strong solvent as described earlier in this disclosure. The first solvent is flowed from the first solvent source 116, through a first solvent line 120 and into a mixer 122. The second solvent is flowed from the second solvent source 118, through a second solvent line 124 and into the mixer 122. The mixer 122 includes at least one mixer inlet and at least one mixer outlet. The mixer 122 establishes a solvent mixture flow stream (or flow path), which flows from the mixer outlet and through a solvent mixture line 130 communicating with a column inlet of the column 104. More than two solvent sources may be provided as noted above.

The sample injection system may include a standard sample injector 386 that is often connected to the autosampler existing in a typical LC system, and may further include one or more features described above for direct injection of sample into the solvent mixture stream downstream of the mixer 122. The sample injector 386 typically includes a multi-port first injection valve 388 communicating with a first sample loop 390, a sample source 334, an injection solvent source 368, and a waste receptacle 392. In the present embodiment, a second injection valve 338 is provided. Ports of the second injection valve 338 communicate with an output line 394 from the first injection valve 388, a fluidic junction 144 in the solvent mixture line 130 via a sample injection line 146, a second sample loop 340 (or buffer loop), and a waste receptacle 160. The second sample loop 340 communicates with a fluid moving device such as a pump 364 (e.g., a syringe pump).

The configuration illustrated in FIG. 3 allows normal operation of the sample injector 386, except that samples are transferred from the first sample loop 390 of the first injection valve 388 to the second sample loop 340 of the second injection valve 338 by operation of the pump 364. The pump 364 may be operated to push the sample from the second sample loop 340 into the solvent mixture stream downstream of the mixer 122 at any desired flow rate, independent of the capabilities of the LC pumping system. Hence, sample injection is done while bypassing the mixer 122, which provides advantages as noted above. In addition, while the sample is being discharged from the second sample loop 340, a new sample may be loaded into the first sample loop 390. In addition, the modifier concentration during sample introduction can be low enough to control any degree of sample band-focusing needed for the application.

In some embodiments, the system 300 may include devices or means for implementing pre-pressurization and use of isolator fluid, as described above and illustrated in FIG. 2.

It will be understood that FIGS. 1 to 3 are high-level schematic depictions of the systems disclosed herein. As appreciated by persons skilled in the art, other components may be included as needed for practical implementations.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the system controller 112 schematically depicted in FIGS. 1 to 3. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the system controller 112 in FIGS. 1 to 3), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for injecting a sample into a flow of a liquid chromatography system, the method comprising:
   providing a flow of a mobile phase in a mobile phase flow path at a mobile phase pressure;
   providing a fluidic junction in the mobile phase flow path, the fluidic junction communicating with a sample injection line and a chromatographic column;
   pressurizing a sample injection flow path, containing a sample, to a pressure matching the mobile phase pressure;
   connecting the sample injection flow path to the mobile phase flow path via the sample injection line and the fluidic junction;
   combining a flow of the pressurized sample injection flow path with the flow of the mobile phase at the fluidic junction to control a degree of sample-band focusing.

2. The method of claim 1, further comprising
   injecting the sample from the sample injection flow path into the fluidic junction and thereby bypassing a solvent mixer.

3. The method of claim 1, further comprising:
   flowing a first solvent and a second solvent into a mixer to form a solvent mixture;
   flowing the solvent mixture into the chromatographic column; and
   while flowing the solvent mixture, injecting the sample into the column downstream from the mixer.

4. The method of claim 3, wherein
   the first solvent is selected from the group consisting of a weak solvent, water, an aqueous buffer fluid, and a supercritical or near supercritical fluid; and
   the second solvent is selected from the group consisting of a strong solvent, an organic solvent, an alcohol, and a polar solvent.

5. The method of claim 1, wherein combining comprises flowing the sample as a plug in front of an isolator fluid.

6. The method of claim 5, wherein the isolator fluid is selected from the group consisting of a highly fluorinated fluid and a perfluorinated fluid.

7. The method of claim 1, comprising loading an injection solvent into an injector valve and loading a sample into a sample loop communicating with the injection valve, wherein injecting comprises pushing the sample from the sample loop.

8. A method for injecting a sample into a solvent mixture path to a separation column of a liquid chromatography system, the method comprising:
   establishing a solvent mixture flow into the column along a solvent mixture flow path at a solvent mixture flow path pressure;
   providing a fluidic junction in the mobile phase flow path, the fluidic junction communicating with a sample injection line and a chromatographic column;
   pressurizing a sample injection flow path, containing a sample, to a pressure matching the solvent mixture flow path pressure;
   connecting the pressurized sample injection flow path to the solvent mixture flow path via the sample injection line and the fluidic junction; and
   controlling a degree of sample-band focusing by controlling a pumping of the sample in the pressurized sample injection flow path into the solvent mixture flow path at the fluidic junction.

9. The method of claim 8, further comprising
   injecting the sample from the sample injection flow path into the fluidic junction and thereby bypassing a solvent mixer.

10. The method of claim 8, wherein establishing a solvent mixture flow comprises:
    flowing a first solvent and a second solvent into a mixer to form a solvent mixture;
    flowing the solvent mixture into the chromatographic column; and
    while flowing the solvent mixture, injecting the sample into the column downstream from the mixer.

11. A system for injecting a sample into a flow of a liquid chromatography system, the system comprising:
    a chromatographic column;
    a syringe configured to dispense a sample;
    a first fluid channel configured to conduct a mobile phase;
    a second fluid channel configured to receive the sample, and communicating with the syringe;
    a junction comprising a first port communicating with the first fluid channel, a second port communicating with the second fluid channel, and a third port communicating with the chromatographic column; and
    a controller configured to control pressurizing the second fluid channel and to control a degree of sample-band focusing by controlling a combining of the flow of the pressurized second fluid channel with a flow of the mobile phase in the first fluid channel, wherein the sample flows with the mobile phase into the chromatographic column.

12. The system of claim 11, further comprising:
a first solvent source;
a second solvent source;
a mixer communicating with the first solvent source via a first solvent line, with the second solvent source via a second solvent line, and with the column via a solvent mixture line; and
an injection valve comprising a sample loop separate from the solvent mixture line and communicating with the junction and an injection solvent source, wherein the injection valve is adjustable to a sample injection position that defines a flow path for an injection solvent through the sample loop and to the junction, such that the injection solvent carries the sample in the sample loop into the solvent mixture line downstream from the mixer and therefore bypassing the mixer.

13. The system of claim 12, further comprising a sample source communicating with the injection valve, wherein the injection valve is adjustable to a sample load position that defines a flow path for a sample to flow into the sample loop.

14. The system of claim 13, further comprising an isolator fluid source communicating with the injection valve, wherein the injection valve is adjustable to an isolator fluid load position that defines a flow path for an isolator fluid to flow into the sample loop, and wherein at the sample injection position the isolator fluid pushes the injection solvent and the sample into the solvent mixture line.

15. The system of claim 11, comprising:
an injection valve for injection of the sample into the second fluid channel; and
the syringe comprises a fluid moving device communicating with the injection valve, wherein the injection valve is adjustable to a pressurizing position at which the fluid moving device pressurizes the sample loop.

16. The LC system of claim 15, comprising a configuration selected from the group consisting of:
a pressure transducer configured for measuring pressure in the sample loop, and a controller configured for controlling the fluid moving device based on pressure measurement signals received from the pressure transducer; and
a first pressure transducer configured for measuring pressure in the sample loop, a second pressure transducer configured for measuring pressure in the solvent mixture line, and a controller configured for controlling the fluid moving device based on comparing pressure measurement signals received from the first pressure transducer and the second pressure transducer.

17. The system of claim 11, wherein the fluidic junction in the solvent mixture line is a first fluidic junction, and further comprising a flow restrictor in the second solvent line and a second fluidic junction between the second solvent source and the flow restrictor, and wherein:
the second solvent source comprises an injection solvent source; and
the flow path defined by the sample injection position runs from the second solvent source, through the sample loop and to the second fluidic junction, such that the second solvent carries the sample into the solvent mixture line.

18. The system of claim 11, wherein the syringe comprises a fluid moving device communicating with the sample loop and configured for selectively pulling fluid into the sample loop and pushing fluid out from the sample loop, and a sample source communicating with the injection valve, wherein the injection valve is adjustable to a sample load position that defines a flow path for the sample to be pulled from the sample source into the sample loop.

19. The system of claim 11, wherein the injection valve is adjustable to an injection solvent load position that defines a flow path for the injection solvent to be pulled from the injection solvent source into the sample loop.

20. The system of claim 11, further comprising
a sample source,
wherein the syringe comprises a fluid moving device communicating with the sample loop and configured for selectively pulling fluid from the sample source into the sample loop and pushing fluid out from the sample loop at the controlled degree of sample-band focusing.

* * * * *